United States Patent [19]

Yasujima et al.

[11] 4,243,882
[45] Jan. 6, 1981

[54] INFRARED MULTILAYER FILM THICKNESS MEASURING METHOD AND APPARATUS

[75] Inventors: Akitaka Yasujima, Yokohama; Naoyuki Shiratori, Tokyo; Shingo Ishikawa, Kawasaki, all of Japan

[73] Assignee: Asahi-Dow Limited, Tokyo, Japan

[21] Appl. No.: 16,754

[22] Filed: Mar. 2, 1979

[30] Foreign Application Priority Data

Mar. 10, 1978 [JP] Japan .................................. 53/266

[51] Int. Cl.³ .............................................. G01J 1/00
[52] U.S. Cl. .................................... 250/339; 250/341; 250/358 R
[58] Field of Search ........... 250/339, 340, 341, 358 R, 250/359, 360; 356/51, 433

[56] References Cited

U.S. PATENT DOCUMENTS

| | | | |
|---|---|---|---|
| 3,405,268 | 10/1968 | Brunton | 250/339 |
| 3,437,811 | 4/1969 | Willis et al. | 250/339 |
| 3,994,586 | 11/1976 | Sharkins et al. | 250/339 |

*Primary Examiner*—Davis L. Willis
*Attorney, Agent, or Firm*—Sughrue, Rothwell, Mion, Zinn and Macpeak

[57] ABSTRACT

A method and an apparatus for measuring the thicknesses of film layers of different synthetic resins forming a composite multilayer film or sheet by utilizing infrared rays. Infrared rays of sample wavelengths, each equal to the infrared absorption wavelength of each film layer, and at least one reference wavelength different from the infrared absorption wavelength of each film layer are projected onto the multilayer film to be measured. Ratios are obtained between the amounts of infrared lights of the sample and reference wavelengths transmitted through the multilayer film. An operation is achieved for solving a simultaneous equation including the ratios and the infrared absorption coefficients of the film layers at the sample and reference wavelengths as coefficients and the thicknesses of the film layers as unknowns, thereby obtaining the thicknesses of the film layers.

21 Claims, 11 Drawing Figures

INFRARED MULTILAYER FILM THICKNESS MEASURING METHOD AND APPARATUS

BACKGROUND OF THE INVENTION

This invention relates to a method and apparatus for measuring the thicknesses of film layers of different kinds of synthetic resins forming a composite multilayer film or sheet by utilizing infrared rays.

For measuring the film thickness of a single-layer plastic film made of a polymer of polyethylene, polypropylene, polyvinyl chloride, polyvinylidene chloride or the like, there have heretofore been employed thickness gauges using $\beta$ rays and infrared rays, and these gauges have been widely used in many industrial fields. However, there have not been proposed effective methods and apparatus for measuring the thicknesses of individually laminated polymer film layers of a composite multilayer film. In the prior art, the cross section of a composite multilayer plastic film (hereinafter referred to as a multilayer film) is enlarged by a microscope or projector to measure the thickness of each film layer of the film by the human eyes. This method is time-consuming and troublesome and subject to measurement errors due to each measuring person's individual difference and incapable of on-line and noncontact measurement, so that the measured values cannot be used as effective process control information. The conventional method presents a problem also in merely measuring the total thickness of the multilayer film. The total thickness value of the multilayer film measured by the $\beta$-ray thickness gauge, usually employed for measuring the single-layer film thickness, do not in some cases agree with the total thickness value measured by a dial gauge, depending upon a combination of polymers of the layers of the multilayer film. The reason is as follows: The $\beta$-ray thickness gauge is to measure the film thickness based on the degree of scattering of $\beta$ rays depending upon the density of the film to be measured. In the case of a multilayer film composed of film layers of different densities, such as a polyethylene (0.9 in density) layer and a polyvinylidene chloride (1.5 in density), even if the total film thickness does not change, the thicknesses of the two film layers vary relative to each other. Since the amount of scattering of $\beta$ rays is determined by the weights that the thicknesses of the respective film layers are multiplied by their densities, the total amount of scattering of $\beta$ rays varies with a change in the thickness ratio of the film layers to provide an erroneous measured value as if the total thickness has changed.

Further, for measuring the multilayer film, it is possible to provide an infrared thickness gauge for a single-layer film for each of the layers of different components or to provide such infrared thickness gauges as one assembly. With this method, however, it is very difficult in practice to measure the thickness of each film layer without being affected by the other film layers. For example, for measuring a multilayer film composed of two layers A and B of different polymers, in the apparatus using conventional infrared single-layer film thickness gauges in combination, three different wavelengths of infrared rays used are selected as follows:

(1) Wavelength $\lambda_R$

A reference wavelength of an infrared ray which is hardly absorbed by either of the film layers A and B.

(2) Wavelength $\lambda_1$

A sample wavelength for the film layer A, which is the wavelength of an infrared ray which is strongly absorbed by the film layer A but hardly absorbed by the film layer B.

(3) Wavelength $\lambda_2$

A sample wavelength for the film layer B, which is the wavelength of an infrared ray which is strongly absorbed by the film layer B but hardly absorbed by the film layer A.

The above three wavelengths are selected and, from the amounts of transmitted infrared lights at the respective wavelengths, the thicknesses of the film layers are measured. Their relationships, expressed for the sake of simplicity, are as follows:

$$I(\lambda_1) = I_0(\lambda_1) e^{-\alpha(\lambda_1)d_A}$$
$$I(\lambda_2) = I_0(\lambda_2) e^{-\alpha(\lambda_2)d_B} \quad (1)$$
$$I(\lambda_R) = I_0(\lambda_R) e^{-\alpha(\lambda_R)(d_A + d_B)}$$

where $I_0(\lambda_1)$, $I_0(\lambda_2)$ and $I_0(\lambda_R)$ are the intensities of infrared lights of the wavelengths $\lambda_1$, $\lambda_2$ and $\lambda_R$ before they enter the film layers A and B to be measured; $I(\lambda_1)$, $I(\lambda_2)$ and $I(\lambda_R)$ are the intensities of infrared lights of the wavelengths $\lambda_1$, $\lambda_2$ and $\lambda_R$ after absorbed by the film layers A and B; $\alpha(\lambda_1)$, $\alpha(\lambda_2)$ and $\alpha(\lambda_R)$ are the infrared absorption coefficients of the film layers A and B at the wavelengths $\lambda_1$, $\lambda_2$ and $\lambda_R$; and $d_A$ and $d_B$ are the thicknesses of the film layers A and B. The infrared ray of the wavelength $\lambda_R$ is scarcely absorbed by the film layers A and B, that is, $\alpha(\lambda_R) = 0$, and in the case where the wavelengths $\lambda_1$, $\lambda_2$ and $\lambda_R$ are close to one another, the infrared radiation may be approximate to $I_0(\lambda_1) = I_0(\lambda_2) = I_0(\lambda_R)$ Accordingly, if $I(\lambda_1)$ and $I(\lambda_2)$ are respectively divided by $I(\lambda_R)$ in the equation (1), it follows that $$\frac{I(\lambda_1)}{I(\lambda_R)} = e^{-\alpha(\lambda_1)d_A} \quad (2)$$
$$\frac{I(\lambda_2)}{I(\lambda_R)} = e^{-\alpha(\lambda_2)d_B}$$

In other words, the ratio between the amounts of film transmitted lights at the wavelengths $\lambda_1$ and $\lambda_R$ corresponds to the thickness $d_A$ through the absorption coefficient $\alpha(\lambda_1)$, the ratio between the amounts of film transmitted lights at the wavelengths $\lambda_2$ and $\lambda_R$ corresponds to the thickness $d_B$ through the absorption coefficient $\alpha(\lambda_2)$.

Therefore, by measuring changes in the two ratios, the thicknesses of the film layers A and B are measured. This is the basic idea of the conventional multilayer film thickness gauge using single-layer film thickness gauges in combination. However, it is very difficult in practice to select the wavelengths $\lambda_1$ and $\lambda_2$ of infrared lights each of which is strongly absorbed by one of the film layers of the multilayer film but hardly absorbed by the other film layer; and even if they can be selected, measurement is limited to multilayer films having film layers of severely restricted combinations of polymers. Further, even if a suitable combination of polymers is obtained, all the wavelengths used may, in a certain case, not lie within the detection wavelength range of one detector, resulting in the necessity of providing detectors of different other kinds. But, owing to the problem of linearity of the sensitivity of each of the detector to the amount of light relative to the other detectors, a change in the sensitivity of each detector with temperature, etc. it is very difficult to obtain an apparatus in practical use. Moreover, the infrared ray of the absorption wavelength peculiar to one film layer is also absorbed by the other film layer, and variations of the thickness of the other film layer exerts an influence upon the amounts of transmitted infrared light of the absorption wavelength for the layer being measured; therefore, the influence between the film layers cannot be removed.

An object of this invention is to provide an infrared multilayer film thickness measuring method and apparatus by which the thicknesses of layers of synthetic resins forming a multilayer film or sheet can be accurately measured in a noncontact manner.

Another object of this invention is to provide an infrared multilayer film thickness measuring method and apparatus by which even if an infrared ray of a sample wavelength for one film layer is also absorbed by other film layers, the thicknesses of the individual film layers can be measured, so that the thickness of each film layer can be accurately measured irrespective of variations of the thicknesses of the other film layers.

Still another object of this invention is to provide an infrared multilayer film thickness measuring method and apparatus with which it is possible to rapidly and accurately measure the thickness of each of film layers of a multilayer film through it.

In accordance with this invention, infrared rays of at least a plurality of sample wavelengths and one or more reference wavelength are projected to a multilayer film or sheet composed of a plurality of film layers made of different synthetic resins. The sample wavelengths each correspond to one of the plurality of different film layers of the multilayer film or sheet and is one of infrared absorption wavelengths of the film layer. Each sample wavelength corresponding to one of the film layers may also coincide with any of the infrared absorption wavelengths of the other film layers; therefore, the infrared absorption wavelengths of each film layer coincide with at least one of the sample wavelengths. The reference wavelength is selected to differ from any of the infrared absorption wavelengths of the respective film layers.

The amounts of infrared lights of each sample wavelength and the reference wavelength which have passed through the multilayer film at least once is normalized by obtaining the ratio between them. The infrared rays of the sample wavelengths and the reference wavelength are projected onto the multilayer film from a projector unit while being switched in a sequential order. The transmitted lights are converted by a photo detector unit to electric signals to derive therefrom respective wavelength components in synchronism with the switching in the projector unit. Alternatively, the infrared rays of only the sample wavelengths and the reference wavelength or infrared rays including those of such wavelengths are simultaneously projected onto the multilayer film and the respective wavelength components are optically separated from the transmitted light and then they are converted by individual photo detector units to electrical signals. The ratios between sample signals which are the thus obtained electric signals representing the intensities of lights of the sample wavelength and a reference signal indicating the intensity of light of the reference wavelength, are respectively taken.

To obtain the transmitted light, the projector unit and the photo detector unit are disposed across the multilayer film to be measured and an infrared ray having passed through the multilayer film once is received by the photo detector unit. In the case where the multilayer film has been deposited on its one side with an infrared ray reflecting layer, such as, for example, an aluminum foil layer, the projector unit and the photo detector unit are both disposed on the side opposite from the reflecting layer of the multilayer film. In this case, the projected infrared ray enters the multilayer film and it is reflected and scattered by the reflecting layer and is then received by the photo detector unit; namely, the infrared ray having twice passed through the multilayer film is received by the photo detector unit. It is also possible to place the projector unit and the photo detector unit on one side of the multilayer film to be measured and a reflector unit on the other side. In such a case, the infrared ray from the projector unit, having passed through the multilayer film, is reflected from the reflector unit back to the direction of incidence to pass through the multilayer film again along the same light path that the incident light followed, and one portion of this reflected light is branched to the photo detector unit. The aforesaid ratios are derived from such a transmitted light transmitted through the multilayer film at least once and received by the photo detector unit.

The thicknesses of the individual film layers are obtained by an operation for solving a simultaneous equation in which the abovesaid ratios, the absorption coefficients of the film layers at the sample and reference wavelengths are used as coefficient and the thicknesses of the film layers are used as unknowns.

For the sake of simplicity, a description will be given in connection with the case where the multilayer film to be measured consists of two film layers A and B made of polymers of different kinds. The film layers A and B both exhibit, in the infrared ray region, infrared absorption spectra having characteristic absorption peaks peculiar to the polymer films, respectively. Now, two arbitrary ones of the absorption peaks are selected and the wavelengths of the selected absorption peaks are represented by $\lambda_1$ and $\lambda_2$, respectively. In this case, it is possible to select as $\lambda_1$ and $\lambda_2$ the wavelengths of infrared lights which are absorbed by the both film layers A and B. The selected wavelength will hereinafter be referred to as the sample wavelengths $\lambda_1$ and $\lambda_2$, respectively. A wavelength of an infrared light which is different from the wavelengths of the abovesaid absorption peaks, that is, which is hardly absorbed by the film layers A and B, is selected as a reference wavelength $\lambda_R$.

Generally, the following equation (3) is formed from an equation of transmission of light:

$$I(\lambda_1) = I_0(\lambda_1) e^{-(\alpha(\lambda_1)d_A + \beta(\lambda_1)d_B)}$$

$$I(\lambda_2) = I_0(\lambda_2) e^{-(\alpha(\lambda_2)d_A + \beta(\lambda_2)d_B)} \quad (3)$$

$$I(\lambda_R) = I_0(\lambda_R) e^{-(\alpha(\lambda_R)d_A + \beta(\lambda_R)d_B)}$$

where $I_0(\lambda_1)$, $I_0(\lambda_2)$ and $I_0(\lambda_R)$ are the intensities of infrared lights incident on the multilayer film at the wavelengths $\lambda_1$, $\lambda_2$ and $\lambda_R$, respectively; $I(\lambda_1)$, $I(\lambda_2)$ and $I(\lambda_R)$ are the intensities of transmitted infrared lights absorbed by the multilayer film at the wavelengths $\lambda_1$, $\lambda_2$ and $\lambda_R$, respectively; $\alpha(\lambda_1)$, $\alpha(\lambda_2)$ and $\alpha(\lambda_R)$ are absorption coefficients peculiar to the film layer A at the wavelengths $\lambda_1$, $\lambda_2$ and $\lambda_R$, respectively; $\beta(\lambda_1)$, $\beta(\lambda_2)$ and $\beta(\lambda_R)$ are absorption coefficients peculiar to the film layer B at the wavelengths $\lambda_1$, $\lambda_2$ and $\lambda_R$, respectively; and $d_A$ and $d_B$ are the thicknesses of the film layers A and B.

Normalizing the ratios between $I(\lambda_R)$ and $I(\lambda_1)$ and between $I(\lambda_R)$ and $I(\lambda_2)$, it follows that $$\frac{I(\lambda_1)}{I(\lambda_R)} = \frac{I_0(\lambda_1)}{I_0(\lambda_R)} e^{-\{(\alpha(\lambda_1)-\alpha(\lambda_R))d_A + (\beta(\lambda_1)-\beta(\lambda_R))d_B\}} \quad (4)$$

$$\frac{I(\lambda_2)}{I(\lambda_R)} = \frac{I_0(\lambda_2)}{I_0(\lambda_R)} e^{-\{(\alpha(\lambda_2)-\alpha(\lambda_R))d_A + (\beta(\lambda_2)-\beta(\lambda_R))d_B\}}$$

Further, taking natural logarithms of the both sides, it follows that $$-\ln\frac{I(\lambda_1)}{I(\lambda_R)} = -\ln\frac{I_0(\lambda_1)}{I_0(\lambda_R)} + \{(\alpha(\lambda_1) - \alpha(\lambda_R))d_A + (\beta(\lambda_1) - \beta(\lambda_R))d_B\} \quad (5)$$

$$-\ln\frac{I(\lambda_2)}{I(\lambda_R)} = -\ln\frac{I_0(\lambda_2)}{I_0(\lambda_R)} + \{(\alpha(\lambda_2) - \alpha(\lambda_R))d_A + (\beta(\lambda_2) - \beta(\lambda_R))d_B\}$$

As is evident from the equation (5), the ratios $I_0(\lambda_1)/I_0(\lambda_R)$ and $I_0(\lambda_2)/I_0(\lambda_R)$ are the ratios of the amounts of incident infrared lights at the respective wavelengths, and hence are constants which remain constant irrespective of variations in the amount of light of the light source.

Therefore, if the values of four absorption coefficients $(\alpha(\lambda_1)-\alpha(\lambda_R))$, $(\beta(\lambda_1)-\beta(\lambda_R))$, $(\alpha(\lambda_2)-\alpha(\lambda_R))$ and $(\beta(\lambda_2)-\beta(\lambda_R))$ are known in advance, it is possible to measure the thicknesses $d_A$ and $d_B$ of the film layers A and B of the multilayer film and its total thickness $d_A+d_B$ by measuring the amounts of film transmitted lights at the wavelengths $\lambda_1$, $\lambda_2$ and $\lambda_R$, taking the ratios $I(\lambda_1)/I(\lambda_R)$ and $I(\lambda_2)/I(\lambda_R)$ and solving a simultaneous quadratic equation in which the thicknesses $d_A$ and $d_B$ are unknowns. The arithmetic processing for the thicknesses is achieved based on the equation (5) and this requires previous setting up of parameters necessary for solving the equation (5). By measuring $I(\lambda_1)$, $I(\lambda_2)$ and $I(\lambda_R)$ in the state of no multilayer film being not provided, the values of $-\ln\{I_0(\lambda_1)/I_0(\lambda_R)\}$ and $-\ln\{I_0(\lambda_2)/I_0(\lambda_R)\}$ are determined. Since these values always remain constant even if a change occurs in the amount of light of the light source, they are set at the beginning of measurement and reset at proper times during measurement. Further, the absorption coefficients $\{\alpha(\lambda_1)-\alpha(\lambda_R)\}$, $\{\beta(\lambda_1)-\beta(\lambda_R)\}$, $\{\alpha(\lambda_2)-\alpha(\lambda_R)\}$ and $\{\beta(\lambda_2)-\beta(\lambda_R)\}$ must be obtained beforehand from the same multilayer film as that to be measured. Once these parameters have been set, by measuring the intensities of transmitted lights $I(\lambda_1)$, $I(\lambda_2)$ and $I(\lambda_R)$ from the multilayer film, the film thicknesses $d_A$, $d_B$ and $d_A+d_B$ can be obtained by the operation in accordance with the equation (5).

As described above, in the present invention, the simultaneous equation (5) is set up without ignoring the infrared absorption of the film layers A and B at the respective wavelengths corresponding thereto and the thicknesses of the film layers are operated based on the equation (5), so that high measurement accuracy can be obtained. Moreover, even if the sample wavelength, for example, $\lambda_1$ coincides with the infrared absorption wavelength of the film layer B which does not correspond thereto, the thicknesses of the film layers can be measured.

For measuring the thickness of the entire area of running multilayer film, it is considered to perform the measurement while reciprocating the measuring apparatus in a direction perpendicular to the direction of travel of the multilayer film, that is, in its widthwise direction. In this case, if the projector unit and the photo detector unit are disposed on both sides of the multilayer film, the optical axis between the projector unit and the photo detector unit becomes out of alignment to cause an error in the measurement unless the positional and angular relationships of the projector unit and the photo detector unit to each other are held constant at all times. For such measurement, it is effective to provide the aforementioned reflector unit and dispose both of the projector unit and the photo detector unit on one side of multilayer film to be measured. As the reflector unit, it is preferred to employ a reflector which reflects the incident light back to the same direction as its direction of incidence, such as a corner cube, a corner cube array, a recurrent reflecting sheet or film. With the provision of such a reflector unit, the projector unit and the photo detector unit can be held as one body on the same side of the multilayer film; therefore, there is no fear of their optical axes getting out of alignment due to their movement and even if a little change occurs in the positional relationships of the projector unit and the photo detector unit to the reflector unit during movement, the incident light is always reflected by the action of the reflector unit back to the same light path, ensuring accurate measurement. In order that the light reflected from the reflector unit and again transmitted through the multilayer film may be branched to the photo detector unit, use may be made of, for example, a half mirror or a right-angled prism. By transmitting the incident light through the multilayer film twice, the absorption by the multilayer film is increased to provide for enhanced SN ratio. Consequently, the two-transmission system is suitable for measuring a film whose infrared absorption is small and is also effective for conducting measurement with the measuring apparatus fixed.

DESCRIPTION OF THE PREFERRED EMBODIMENTS

Figure 1:
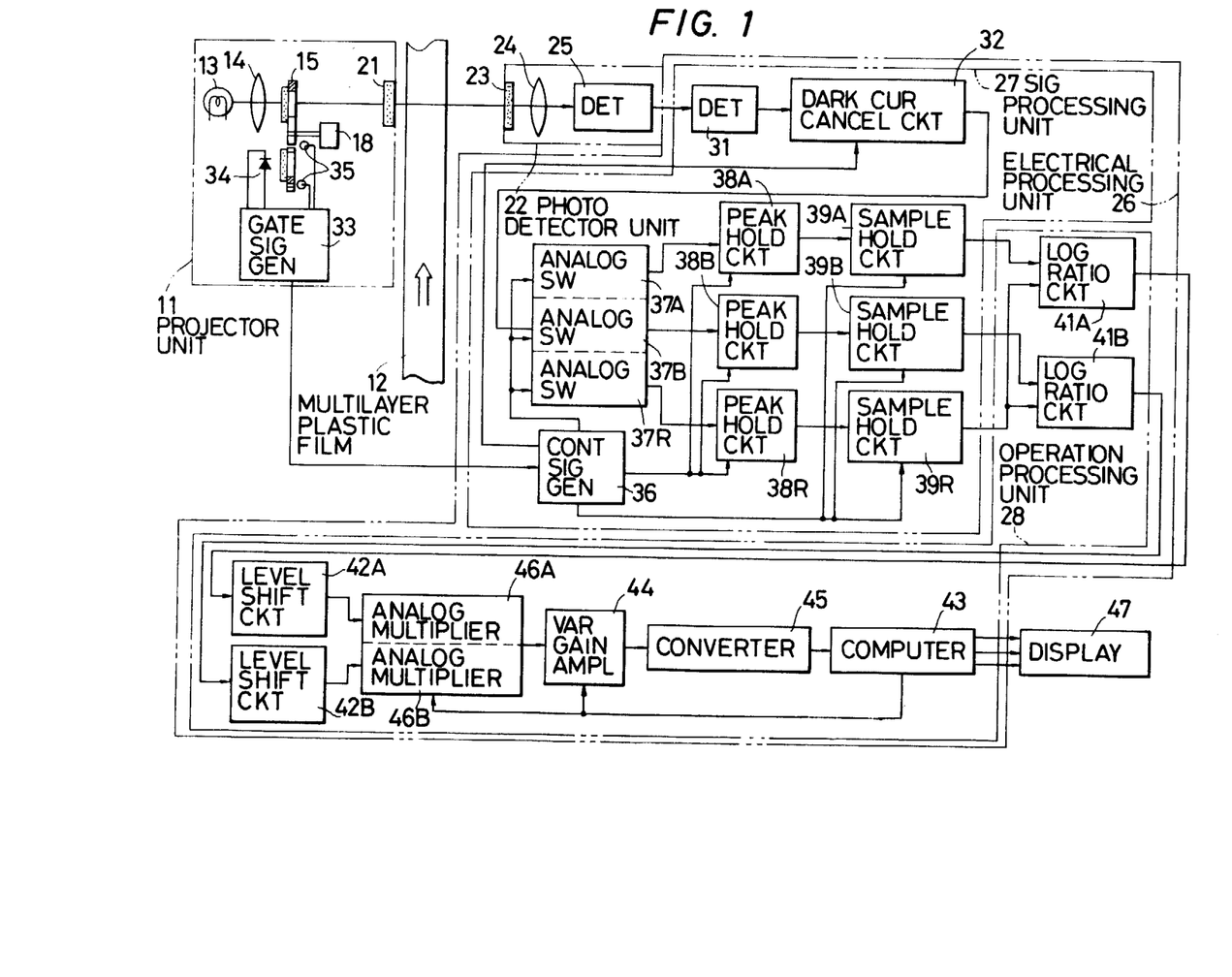
FIG. 1 is a block diagram illustrating an embodiment of an infrared multilayer film thickness measuring apparatus of this invention.

FIG. 1 illustrates an embodiment of this invention, in which infrared rays of a plurality of sample wavelengths and a reference wavelength are projected, on a time divided basis, from a projector unit 11 to a multilayer plastic film 12 to be measured. In the projector unit 11, there is provided an infrared radiation light source 13 for generating infrared rays stabilized in light intensity with the lapse of time. The light source 13 is suitably selected from a group consisting of a tungsten lamp, a halogen lamp, a nichrome wire heater, a glow bar, etc. in accordance with the wavelengths of infrared rays used. In a region of infrared rays of wavelengths longer than 2.5 μm, the tungsten and halogen lamps are not effective infrared radiation light sources because of infrared absorption by their glass envelopes; and for such long wavelengths, the nichrome wire heater and the glow bar are desirable. The infrared rays emitted from the light source 13 are rendered by a lens system 14 into a pencil of parallel light rays. The lens system 14 is suitably selected from a group consisting of a quartz lens, a germanium lens, a silicon lens, etc. in dependence upon the wavelength of infrared rays used. The infrared rays thus rendered by the lens system 14 into the pencil of parallel light rays enter a light chopper 15.

Figure 2:
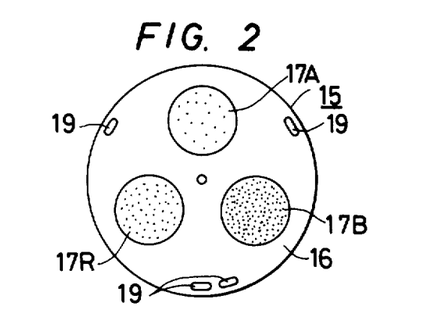
FIG. 2 is a front view showing an example of a light chopper for use in this invention.

The light chopper 15 is a disc 16 such, for example, as shown in FIG. 2, which is made of a material inhibiting the passage therethrough of infrared rays and has three narrow-band, infrared band-pass interference filters 17A, 17B and 17R which are fitted into circular holes in the disc 17, with their centers lying on the same circumference at equiangular intervals. The light chopper 15 is driven by a synchronous motor 18, as shown in FIG. 1, and the infrared rays passing through the lens system 14 are incident on the rotational positions of the band-pass filters 17A, 17B and 17R. By the rotation of the light chopper 15, the infrared rays incident thereon pass through the narrow-band infrared band-pass interference filters on a time-series basis. The disc 16 of the light chopper 15 has made therein small holes 19 to obtain signals indicating its rotation. FIG. 2 shows an example of the light chopper for measuring the thicknesses of two kinds of film layers A and B forming a multilayer plastic film. In this example, three narrow-band infrared band-pass interference filters are mounted on the disc 16, for producing monochromatic lights of infrared rays which are necessary for obtaining the thicknesses of the individual film layers. The filters 17A and 17B are those filters of sample wavelengths $\lambda_1$ and $\lambda_2$ which have as their center transmission wavelengths the wavelengths of infrared rays respectively absorbed by the film layers. The remaining filter 17R is a filter of a reference wavelength $\lambda_R$ which has as its center transmission wavelengths the wavelength of infrared rays which are scarcely absorbed by the film layers A and B. The three wavelengths are selected in consideration of the infrared absorption spectra of the film layers A and B, the infrared radiation source, detectors, etc. so that the thicknesses of the individual film layers of the multilayer film 12 can be measured with high accuracy. FIG. 2 shows the light chopper 15 for measuring the thicknesses of two kinds of film layers A and B making up the multilayer film. In the case of measuring the thicknesses of three or more film layers forming a multilayer film, wavelengths fit for the measurement are selected and the numbers of filter receiving holes of the light chopper, sample narrow-band infrared band-pass interference filters and reference narrow-band infrared band-pass interference filters are increased corresponding to the numbers of kinds of laminated film layers of the multilayer film.

The monochromatic infrared rays separated by the light chopper 15 on the time-series basis are applied to a wide-band infrared interference filter 21 to remove an influence of ambient light.

The infrared rays emitted from the projector unit 11, that is, the infrared rays having passed through the filter 21 are projected on the multilayer film 12 to be measured, which is at a standstill or continuously running. In this example, the film layers A and B made of two different polymers are laminated. Not only in the case of the two film layers A and B being laminated but also in the case of three film layers being laminated in order of A-B-A or four or more film layers A and B being laminated alternately with each other, the sums of the thicknesses of the individual film layers A and B are similarly measured. The individual monochromatic infrared rays of the wavelengths $\lambda_R$, $\lambda_1$ and $\lambda_2$, such as shown in FIG. 3 (1), are projected to the multilayer film 12 via the same optical path on the timeseries basis.

The infrared rays having passed through the multilayer film 12 are each received by a photo detector unit 22 for conversion to an electric signal proportional to the intensity of light of the infrared rays received. In the photo detector unit 22, the incoming transmitted rays of light are directed to a wide-band infrared interference filter 23 which permits the passage therethrough of the transmitted infrared rays absorbed by the individual film layers making up the multilayer film 12 and by which external rays of light are removed from the transmitted rays of light. The thus transmitted rays of light are then focused by a lens system 24 into a beam. The lens system 24 is suitably selected as is the case with the aforesaid lens system 14. The beam of infrared rays focused by the lens system 24 is detected by a detector 25 as an electric signal corresponding to the intensity of light of the infrared rays. The detector 25 may be a PbS (lead sulfide) detector, a PbSe (lead selenate) detector, a pyro-detector or various semiconductor detectors cooled by a liquid air. These detectors are selectively employed in consideration of the wavelength region of infrared rays to be detected.

The signal indicating the intensity of infrared rays, thus derived from the photo detector unit 22 is separated by an electrical processing unit 26 into sample signals of the components of the sample wavelengths $\lambda_1$ and $\lambda_2$ and a reference signal of the components of the reference wavelength $\lambda_R$ and, at the same time, the ratios of the sample signals to the reference signal are obtained. In the electrical processing unit 26, an operation is achieved for obtaining the thicknesses of the film layers A and B by solving a simultaneous equation in which the abovesaid ratios and the absorption coefficients in the sample wavelengths and the reference wavelength are coefficients and the thicknesses of the film layers A and B are the unknown quantities. In the present embodiment, the peak values of the signals with respect to the respective wavelength components are detected first in a signal processing unit 27 and then, in an operation processing unit 28, the abovesaid ratios are obtained on the basis of the detected peak values and the operation for solving the simultaneous equation is carried out.

Figure 3:
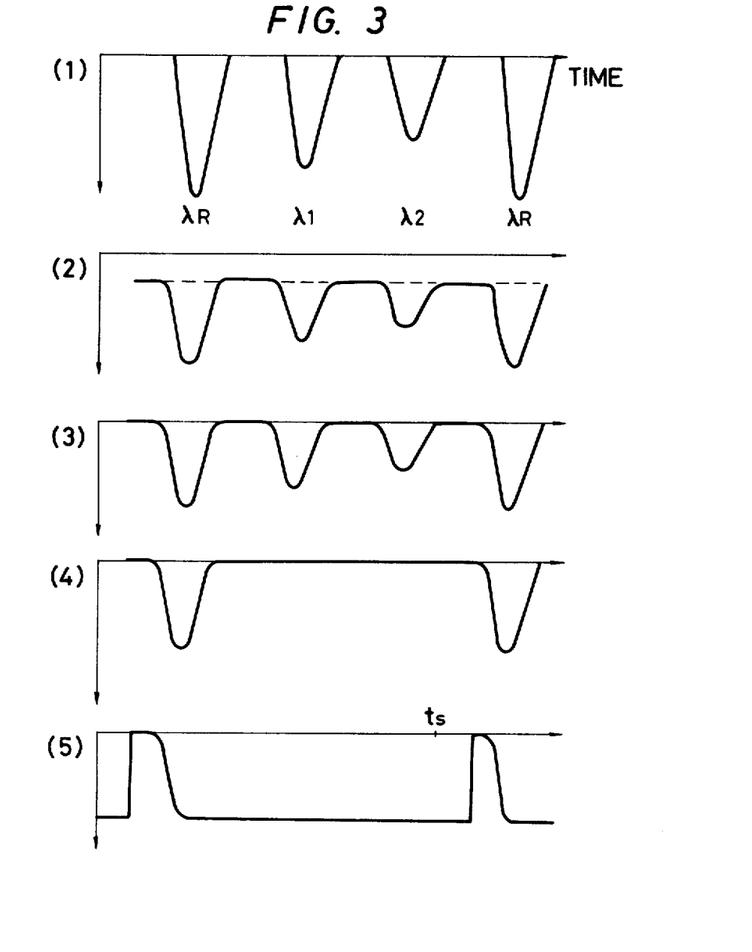
FIG. 3 shows waveforms appearing at respective parts in FIG. 1.

In the signal processing unit 27, the output from the detector 25 is applied, as needed, to a detector circuit 31 of a constant-current system which yields a linear output in response to a change in the intensity of received infrared rays, thereby providing such an output signal as shown in FIG. 3(2). This output signal is provided to a dark current cancel circuit 32 to remove from the output signal a dark current corresponding thereto. That is, in the detector 25 a current flows even when no infrared rays are received from the light source 12. This current is called a dark current and varies with temperature, ambient light, external noises, etc. But such a dark current cancel circuit 32 provides only the signal components proportional to the variation in the light intensity. As the dark current differs for each wavelength, the dark current cancel circuit 32 is controlled in synchronism with the reception of light of each wavelength.

As a consequence, a gate signal is produced by a gate signal generator 33 in synchronism with the generation of each of the monochromatic infrared rays in the projector unit 11. The gate signal is provided, for example, as follows: A light emitting device 34, such as a lamp, a light emitting diode or the like, is disposed on one side of the light chopper 15, while on the other side photo diodes, photo transistors or like photo detectors 35 are placed respectively in opposing relation to the small holes 19 of the light chopper 15. The photo detectors 35 are connected to the gate signal generator 33 to derive therefrom a gate signal synchronized with the passage of infrared rays through each of the filters 17A, 17B and 17C. The gate signal is provided to a control signal generator 36.

The dark current cancel circuit 32 derives therefrom, for example, such an output as shown in FIG. 3(3). This output is supplied to analog switches 37A, 37B and 37R, which are repeatedly controlled by the control signal generator 36 in a sequential order, supplying peak hold circuits 38A, 38B and 38R with detection signals at the wavelengths $\lambda_1$, $\lambda_2$ and $\lambda_R$, respectively. As a result of this, only that signal in the output from the dark current cancel circuit 32 (FIG. 3(3)) corresponding to the reference wavelength passes through an analog switch 37R to the peak hold circuit 38R, as shown in FIG. 3(4), to derive therefrom such an output as depicted in FIG. 3(5). The peak hold circuit 38R holds the peak value of the signal supplied after being reset. In a likewise manner, those signals in the output from the dark current cancel circuit 32 corresponding to the wavelengths $\lambda_1$ and $\lambda_2$ are respectively held in the peak hold circuits 38A and 38B. Thus, the two sample signals and the reference signal which are detected output respectively corresponding to the wavelengths $\lambda_1$, $\lambda_2$ and $\lambda_R$ are separated from one another.

The peak hold circuits 38A, 38B and 38R hold the peak values of the respective signals until the next signals are applied thereto and at least immediately before the application of new signals thereto, these peak hold circuits of new signals thereto, these peak hold circuits are reset to hold the peak values of the new signals. Accordingly, the peak values held by these circuits are updated for each rotation of the light chopper 15. The peak value voltages respectively held by the peak value hold circuits 38A, 38B and 38R are simultaneously sampled, for example, at a moment $t_s$ immediately before the reference signal is updated, as shown in FIG. 3(5), and the sample values are respectively held by sample hold circuits 39A, 39B and 39R.

The thus obtained two sample signals and one reference representing the intensities of the infrared rays of the wavelengths $\lambda_1$, $\lambda_2$ and $\lambda_R$ are supplied to the processing unit 28. In the processing unit 28, the outputs from the sample hold circuits 39A and 39B are respectively applied to log ratio circuits 41A and 41B, which are supplied with the output from the sample hold circuit 39R in common to them. In the log ratio circuit 41A, a ratio is taken between the sample signal voltage corresponding to the amount of the film transmitted light of the wavelength $\lambda_1$ and the reference signal voltage corresponding to the amount of the film transmitted light of the wavelength $\lambda_R$ and the ratio is further transformed to a common logarithm (log). In the log ratio circuit 41B, a similar ratio is taken between the sample signal voltage corresponding to the amount of the film transmitted light of the wavelength $\lambda_2$ and the reference signal voltage corresponding to the amount of the film transmitted light of the wavelength $\lambda_R$ transformed to a common logarithm (log). The reason for taking the ratios of the sample signals to the reference signal is to standardize the sample signals of the wavelengths $\lambda_1$ and $\lambda_2$ with the references of a change in the amount of light from the light source 13 and scattering and reflection of light on the surface of the multilayer film 12, thereby enhancing and stabilizing the film thickness measurement accuracy for a long time. Further, the reason for the logarithmic transformation is that since the values of transmission factors at the wavelengths $\lambda_1$ and $\lambda_2$ do not bear, as they are, linear relationships to the film thicknesses, the logarithms of the transmission factors obtained by the logarithmic conversion linearly correspond to the film thicknesses, as seen from the aforementioned equation (5). Although natural logarithms are taken in the equation (5), the above embodiment is described with regard to the case of taking the common logarithms since elements for the transformation to common logarithms are now commercially available. As natural and common logarithmic transformed values are proportional to each other, either of the natural and the common logarithmic conversion may be used in this invention.

The outputs from the log circuits 41A and 41B are provided to level shift circuits 42A and 42B, respectively. In the absence of the multilayer film 12, if $I_o(\lambda_1)$ and $I_o(\lambda_R)$ or $I_o(\lambda_2)$ and $I(\lambda_R)$ are equal to each other, as seen in the equation (5), that is, if the infrared rays of the respective wavelengths are of the same intensity, the first terms of the right side of the equation (5) becomes zero and since the multilayer film 12 is not disposed between the projector unit 11 and the photo detector unit 22, the second term of the abovesaid right side is naturally zero, so that the amount of light being measured, i.e. the left side of the equation (5) naturally becomes zero and the log ratio circuits 41A and 41B provide no outputs. In practice, however, owing to the wavelength dependency of the radiation intensity of the light source 13 and dispersion in the infrared light transmissivity of each of the filter used, the chromatic infrared rays as the incident lights of the three wavelengths are not always equal in intensity of light, for instance, as depicted in FIG. (1). Therefore, also in the absence of the multilayer film 12, i.e. in the case of 100 percent transmission, the first term of the right side of the equation (5) remains as a constant term. Consequently, the intensity of light after transmission through the film, which is the quantity actually measured, that is, the left side of the equation (5), always corresponds, in the form jacked up by the constant part, to the film thickness, i.e. the second term of the right side of the equation (5). In view of this, prior to measurement of the thickness of the multilayer film 12, the voltage corresponding to the constant term, which is yielded in the case of the multilayer film 12 being not arranged, is cancelled by shift level circuits 42A and 42B, by which the outputs from the level shift circuits 42A and 42B are so set as to be always zero in the absence of the multilayer film 12. By measuring the thickness of the multilayer film 12 after this setting, the common logarithmic ratio of the transmission factors of the amounts of the transmitted lights absorbed by the multilayer film 12, that is, the left side of the equation (5) linearly corresponds to the film thickness.

In this way, the constant term of the equation (5) is removed by the level shift circuits 42A and 42B to provide signals linearly corresponding to the film thickness. These signals are, if necessary, amplified for input to a computer 43. In this embodiment, analog multiplexers 46A and 46B are provided for processing the two output signals from the level shift circuits 42A and 42B by one common variable gain amplifier 44 and an analog-digital converter 45. The multiplexers 46A and 46B are placed under the control of the computer 43. In the case of providing a variable gain amplifier and an analog-digital converter for the exclusive use of each of the output signals from the two level shift circuits 42A and 42B, such switching circuits need not be employed. In the variable gain amplifier 44, the input thereto is amplified by the control of the computer, to its input level. The amplified output is converted by the analog-digital converter 45 to digital form. As the converter 45, for enhancement of the measurement accuracy, use is made of an analog-digital converter having a large number of bits, preferably, twelve or more bits. The computer 43 is a microcomputer or minicomputer and in the case of the multilayer film 12 being two-layer, the thicknesses $d_A$ and $d_B$ of the respective film layers are calculated by processing the simultaneous quadratic equation in which the left sides of the two equations shown by the equation (5) are used as known measurement data, the absorption coefficients of the respective film layers at the wavelengths $\lambda_1$, $\lambda_2$ and $\lambda_R$ are used as coefficients and the film thicknesses $d_A$ and $d_B$ are used as unknown quantities. The calculation results are displayed on a known suitable display 47, such as a printer, meter, X-Y recorder or the like.

Figure 4:
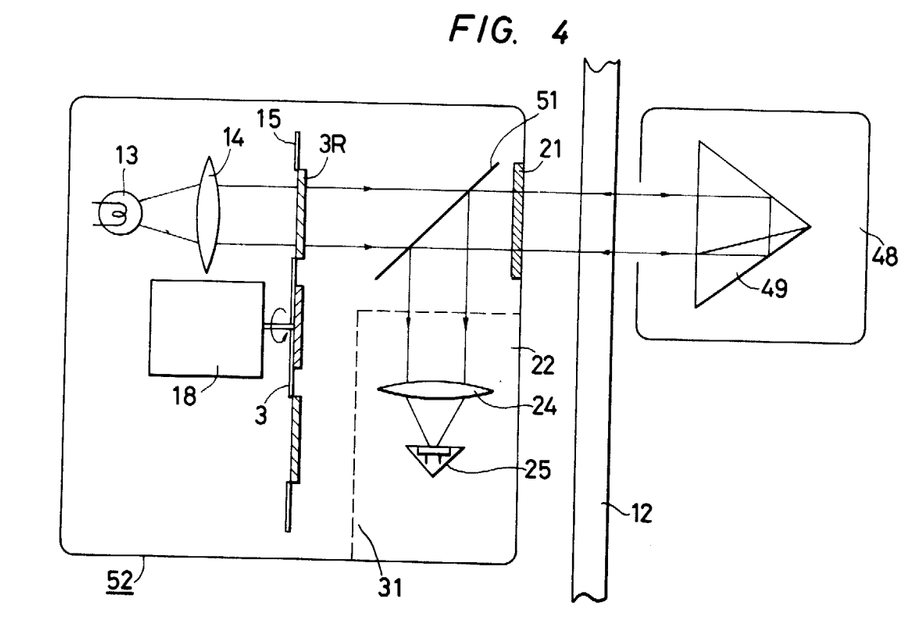
FIG. 4 is a block diagram illustrating one part of the infrared multilayer film thickness measuring apparatus of this invention using a reflector unit.

In the above embodiment, the projector unit 11 and the photo detector unit 22 are disposed across the multilayer film 12 to be measured and the light once transmitted through the multilayer 12 is received by the photo detector unit 22, it is also possible to provide a reflector unit and dispose the projector unit 11 and the photo detector unit 22 on one side of the multilayer film 12 so that infrared rays having twice passed through the multilayer film 12 are received by the photo detector 22. An example of such an arrangement is illustrated in FIG. 4, in which parts corresponding to those in FIG. 1 are identified by the same reference numerals. In this embodiment, a reflector unit 48 is provided in opposing relationship to the projector unit 11 across the multilayer film 12. The chromatic infrared rays emitted from the projector unit 11 are projected to the multilayer film 12 and the transmitted light therefrom is incident on the reflector unit 48. The reflector unit 48 is, for example, a corner cube 49, which reflects the incident light on the same path as the incident light path. Accordingly, the transmitted light having entered the reflector unit 48 is reflected back to the projector unit 11 through the same region in the multilayer film 12 that the transmitted light has passed. Since this incident light follows up the same light path that the light from the light source 13 in the projector unit 11 to the multilayer film 12 takes, a branching unit 51 is provided for directing the reflected light to the photo detector unit 22. As the branching unit 51, the so-called half mirror is disposed, for instance, between the wide-band, infrared ray interference filter 21 and the light chopper 15; and at least one portion of the transmitted light from the infrared interference filter 21 is reflected by the half mirror, that is, branched to the photo detector unit 22. The arrangements of the stages following the photo detector unit 22 are identical with those in the embodiment shown in FIG. 1. With the arrangement employing such an optical system, the photo detector unit 22 is placed in the same case 52 together with the projector unit 11 and they are fixed relative to each other. As a consequence, even if the positional and angular relationships between the reflector unit 48 and the projector unit 11 are a little incorrect, the reflected light from the reflector unit 48 always takes the same light path as the incident light path, so that in the case of the projector unit 11 and the reflector unit 48 being simultaneously shifted for measurement, even if they are a little inaccurate in the abovesaid relationships, accurate measurement takes place.

The reflector unit 48 is not a mere plane mirror but may be a corner cube, a corner cube array or an assembly of recurrent reflection sheets or recurrent reflection sheets or like optical elements.

The corner cube may be one that is employed, for example, as a reflector of a laser distance measuring apparatus, that is, a three-faced, right-angled triangular cube in the form of a glass cube having its one corner cut off. Further, use may be made of a hollow type corner cube that three plane mirrors are held at right angles to one another just like three coordinate planes of rectangular coordinates. The material for the corner cube must be selected in accordance with the range of wavelengths of the infrared rays used. Especially, in the case of the wavelength range below about 2.5 $\mu$m, a solid corner cube as of quartz, optical glass or the like is preferred; and in the case of the wavelength range above about 2.5 $\mu$m, it is preferred to use a solid corner cube made of infrared glass or germanium or silicon crystal or a hollow corner cube composed of three plane mirror. The corner cube is preferred to be as large as possible but, because of a problem of the fabrication accuracy, cannot be made so large; the corner cube must be of such a size that its plane of incident may sufficiently cover at least the diameter of the pencil of incident light rays. What is further taken into consideration is that since a solid corner cube as of quartz inevitably has a surface of incidence, the incident light is reflected a little by the plane of incidence; namely, the plane of incidence serves as a plane mirror. In the case where the corner cube is a little inclined with respect to the pencil of incident light rays, the light having passed through the plane of incidence is mostly reflected from the three planes of the corner cube perpendicular to one another back to the same direction as that of incidence by virture of the essential function of the corner cube, but a small amount of light reflected from the surface of incidence is not reflected back to the direction of incidence. As a result of this, the light reflected from the surface of incidence of the corner cube is led to the detector 25 of the photo detector unit 22 to appear as an optical axis deviation, which partly constitutes a factor in errors. To prevent that the reflected light from the plane of incidence is led to the detector 25 of the photo detector unit 22, it is necessary to dispose the corner cube with its plane of incidence a little inclined to the optical axis or employ a corner cube having a slightly inclined plane of incidence in place of a regular tetrahedral corner cube, a corner cube covered with a nonreflecting coating or a hollow corner cube composed of three planar mirrors and having no surface of incidence.

Though a little low in accuracy, use can also be made of a corner cube array of molding of plastic, glass, etc. which is generally used, for example, as a traffic-control sign or a sticker to be plastered on the rear end of an automobile for intensely reflecting light of a head lamp of a succeeding automobile back to the direction of its driver to make him recognize the presence of the automobile running ahead. A reflecting element that fine glass or plastic beads of high refractive index are made spherical lenses and innumerably embedded in a metal film serving as a light reflecting layer, such as generally known under the name of a recurrent reflecting sheet or film, also reflects an incident light back to the same direction as that of incidence. This reflecting member is inferior to the corner cube in terms of accuracy, of course, but improves the problem of measurement error due to nonuniform running of measuring heads, as compared with the embodiment of FIG. 1 which does not employ the reflector unit 48. What must be noted here, however, is that when employing such a recurrent reflecting optical element made of plastic, its reflection spectrum in the infrared region should be studied in some cases. In short, as the reflector unit 48, any other optical systems than the abovesaid ones may also be used if they reflect incident infrared rays accurately back to the direction of incidence.

Figure 5:
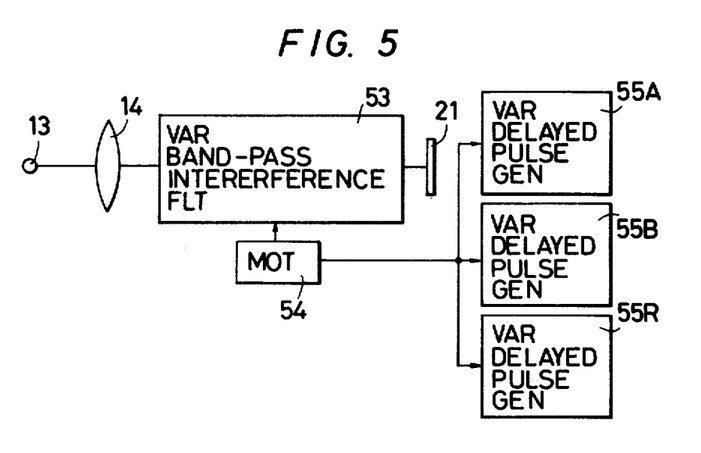
FIG. 5 is a block diagram showing one part of an example of this invention employing a variable transmission wavelength infrared band-pass filter.

The light separating means for separating infrared rays into monochromatic lights in the projector unit 11 may be such an arrangement that a disc on which infrared narrow-band interference filters, each permitting the passage therethrough of light of a particular wavelength, are mounted as many as wavelengths necessary for measurement is rotated to obtain infrared rays of a desired one of the wavelengths on a time-series basis. In this case, it is also possible to align such filters on a disc and reciprocate the disc across the infrared ray path at right angles thereto. Further, the light separating function can also be achieved by changing the wavelength of the infrared monochromatic light by the employment of a variable-transmission-center-wavelength, infrared narrow-band interference filter whose transmission center wavelength continuously changes. The light separating means which continuously changes its transmission center wavelength is needed in the case of a general purpose film thickness gauze for measuring a multilayer composed of polymers of various compositions. For example, as illustrated in FIG. 5, infrared rays having passed through the lens system 14 are applied to a variable-transmission-center-wavelength, narrow-band infrared band-pass interference filter 53 and the transmitted light therefrom is projected to the wide-band infrared filter 21. The filter 53 is one that a continuously variable-wavelength optical filter is mounted on a sectorial substrate, such as, for example, a filter placed on the market under the name of an infrared circular variable filter. By rotating this sectorial filter to change the position of light directed thereto, a monochromatic light whose wavelength continuously varies can be obtained. The transmission center wavelength is changed in succession by rotating the filter 53 with a motor 54.

For each rotation of the motor 54, pulses are produced to drive variable delayed pulse generator 55A, 55B and 55R, deriving therefrom pulses respectively delayed for preset periods of time. The pulses are applied, for example, to the analog switches 37A, 37B and 37R in FIG. 1 to control them to obtain therefrom the outputs of the photo detector unit 22 which correspond to the transmitted lights of the wavelengths corresponding to the delayed pulses, respectively. The variable delayed pulse generators 55A, 55B and 55R are each comprised, for example, of a variable time constant monostable multivibrator and a constant pulse width monostable multivibrator which is driven by the trailing edge of the output pulse therefrom. Accordingly, by changing the delay times of the delayed pulse generators 55A, 55B and 55R, measurement can be achieved with a variety of sample and reference wavelengths.

Further, in the event that the sample wavelengths and the reference wavelength are close to one another, a required number of infrared monochromatic lights can be obtained by the use of only one narrow-band, infrared band-pass interference filter. That is, by changing the angle of incidence of a unseparated infrared light to the interference filter, the center of transmission wavelength of the filter shifts towards shorter wavelengths than that in the case of perpendicular incidence, so that a plurality of infrared monochromatic lights of discontinuously or continuously varying wavelengths can be produced. By changing the angle of incidence from 0° to about 70°, the center transmission wavelength of the filter is shifted towards shorter wavelengths about 5 to 7% of the center transmission wavelength in the case of perpendicular incidence (0°). Therefore, when the wavelengths of a plurality of infrared rays necessary for measurement are close to one another, a plurality of infrared monochromatic lights can be obtained by using one interference filter whose center transmission wavelength at the time of perpendicular incidence is equal to the longest one of the wavelengths of the incident infrared rays and by changing the angle of incidence of the infrared rays to the filter relative to each other. The angle of incidence can be changed by rotating or reciprocating the interference filter with a motor or the like. The required wavelengths may be selected in the manner described previously. Moreover, a diffracting grating or prism can also be employed for continuously changing the wavelength of infrared rays.

Figure 6:
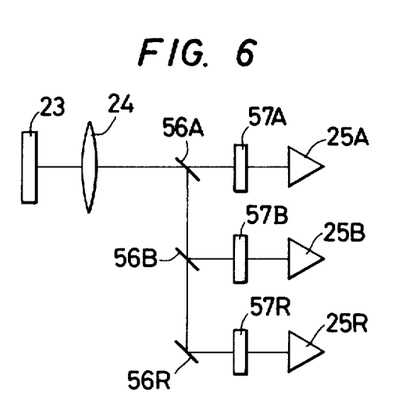
FIG. 6 is a block diagram showing one part of another example of this invention using a plurality of detectors.

The infrared rays of the sample and reference wavelengths can also be obtained on a time-series basis not only on the side of the projector unit 11 but also on the side of the photo detector unit 22. That is, in the projector unit 11, infrared rays of all wavelengths over a certain range are projected onto the multilayer film 12 and, in the photo detector unit 22, the light chopper 15 shown in FIG. 2 is rotated in front of the detector 25, whereby to pick up the sample wavelength components and the reference wavelength components. This may also be achieved by providing in the photo detector unit 22 a variable filter which is capable of continuously changing its pass band, such as described previously with regard to FIG. 3. In the above, the detector 25 of the photo detector 22 is used in common to the sample and reference wavelengths, but it is also possible to employ such a detector for each of the sample and reference wavelengths, for example, as illustrated in FIG. 6. In such a case, the transmitted light from the multilayer film 12, after having passed through the wide-band filter 23 and the focusing lens system 24, is branched by half mirrors 56A and 56B one after the other and the branched lights are applied to filters 57A, 57B and 57R to derive therefrom lights of the sample wavelengths and the reference wavelength, respectively, which are then applied to separate detectors, 25A, 25B and 25R to detect the components of the wavelengths $\lambda_1$, $\lambda_2$ and $\lambda_R$, respectively. Reference 56R indicates a mere mirror. What is necessary for processing the outputs from the detectors 25A, 25B and 25R is only to provide the detector 31 and the dark current cancel circuit 32 for each of the detector outputs in the signal processing unit shown in FIG. 1. The provision of the detector for each wavelength necessitates uniform sensitivity characteristics of the respective systems, and therefore, it is easier to employ the detector in common as shown in FIG. 1.

Where the multilayer film 12 is coated over its one surface with paper or aluminum, the projector unit 11 and the photo detector unit 12 on the side opposite from the coated surface of the film 12, as depicted in FIG. 4. As the computer 43, an analog computer can be used solely or in combination with a digital computer. In the case of employing a microcomputer or minicomputer, the entire processing of the electrical processing unit can also be conducted by the computer. For example, as regards the peak detection, the input signal from the photo detector unit 22, such as shown in FIG. 3(2), is compared with the width of its waveform and sampled at sufficiently short intervals, and each sampled value is inputted in digital form to the computer, in which it is compared with the immediately preceding sampled value, and when the current sampled value becomes smaller than the immediately preceding one, the latter is stored in a memory as a peak value for the wavelength components. The following waveforms are also similarly processed to obtain the peak values of the detected outputs of the wavelengths $\lambda_1$, $\lambda_2$ and $\lambda_R$. The peak values thus obtained are normalized by the value peak of the reference signal and their logarithmic operations are conducted and, further, an operation is performed for solving the aforesaid simultaneous equation. In this case, the output from the gate signal generator 33 is provided to the computer so as to enable it to judge which one of the wavelength signal is being processed. The absorption coefficients of the respective film layers at the wavelengths $\lambda_1$, $\lambda_2$ and $\lambda_R$ are prestored in a memory of the computer 43 in the case of conducting the measurement of multilayer films of the same kind. These absorption coefficients may also be inputted for each measurement.

The foregoing description has been given of the case where the multilayer film is composed of two different polymers. Also in the case of the multilayer film being composed of three or more polymer film layers, the film thicknesses of individual film layers can be obtained by selecting three or more sample wavelengths and one or more reference wavelengths and setting up simultaneous equations of the same number as unknowns and performing arithmetic processings of the equations. Needless to say, care should be taken not to select such a combination of wavelengths that a combination of the absorption coefficients of the polymers makes the solution of the simultaneous equations unstable or impossible. That is, such an unwanted selection must be avoided that the ratio between $\{\alpha(\lambda_1)-\alpha(\lambda_R)\}$ and $\{\beta(\lambda_1)-\beta(\lambda_R)\}$ becomes equal to the ratio between $\{\alpha(\lambda_2)-\alpha(\lambda_R)\}$ and $\{\beta(\lambda_2)-\beta(\lambda_R)\}$, for example, in the case of the binary system.

The above-described infrared multilayer film thickness measuring method and apparatus of this invention produces the following effects.

Figure 7:
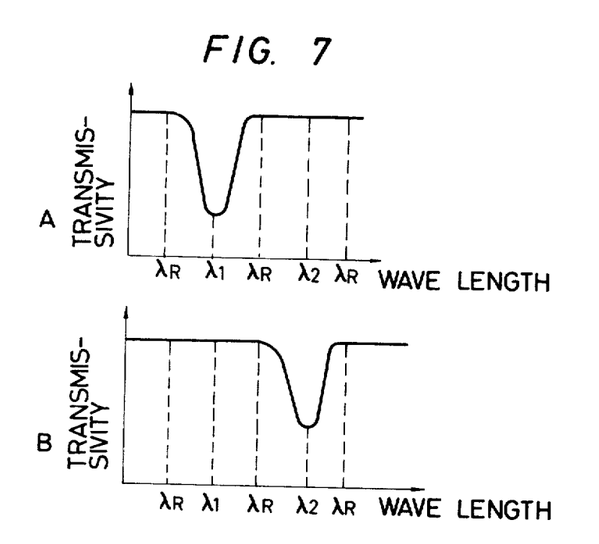
FIGS. 7 to 10 are graphs showing the relationships of infrared absorption wavelengths of film layers A and B to sample and reference wavelengths.
Figure 8:
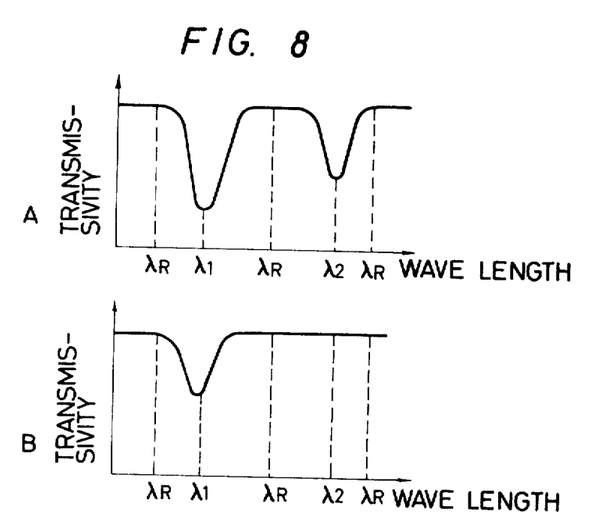
Figure 9:
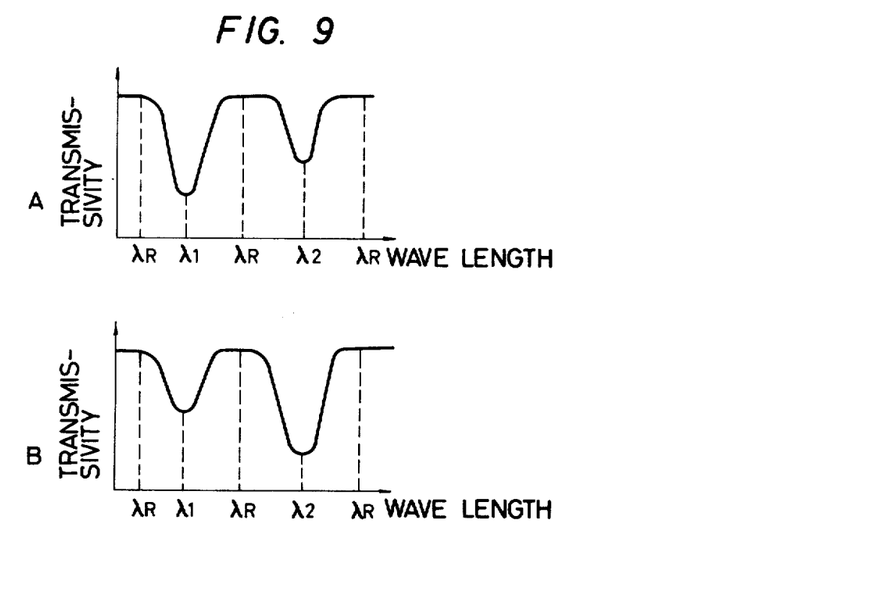
Figure 10:
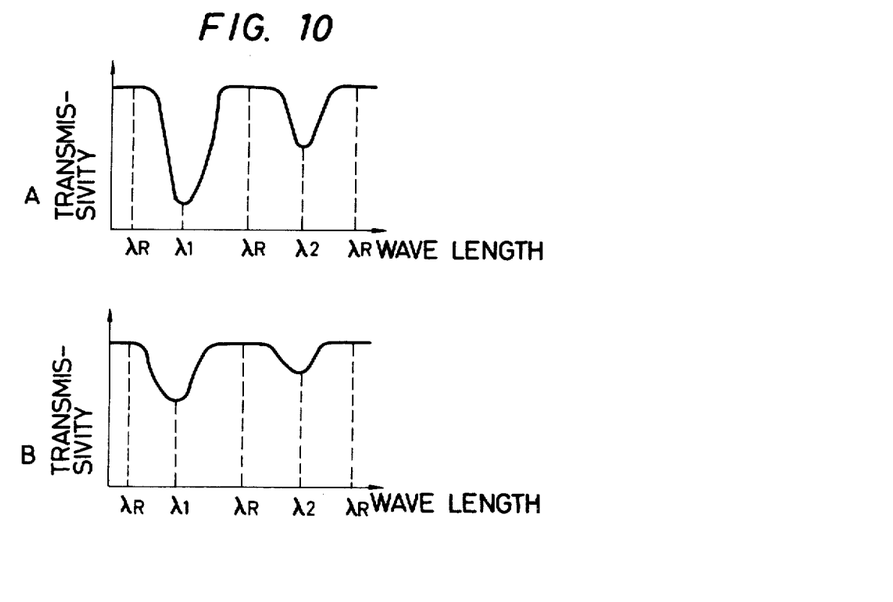

It is in the case where the film layers A and B each have such an infrared spectrum as shown in FIG. 7 that their thicknesses can be measured by a mere combination of conventional single-layer film thickness gauges for the selection of the wavelengths of infrared rays necessary for measurement. That is, it is the case where the one of the film layers scarcely absorbs the infrared rays at the wavelength at which the other film layer largely absorb the infrared rays. In connection with an actual multilayer film, however, it is appreciably difficult to select such a combination of wavelengths; therefore, such a type of multilayer thickness gauge is far from practical use and, even if possible, its use is limited specifically to multilayer films employing limited combinations of polymers. This invention allows ease in the selection of combination of wavelengths severely limited in the prior art and, by operating such simultaneous equations as mentioned previously, the thicknesses of the both film layers can be obtained with no problem occurring even if the one of the film layers absorbs infrared rays at the wavelength where the other film layer largely absorbs the infrared rays. That is, in the present invention, the film thicknesses can be measured also in the cases of such combinations of wavelengths as shown in FIGS. 8A, 8B, 9A, 9B and 10A, 10B, respectively. FIG. 8 shows the case where the both film layers absorb infrared rays at one wavelength $\lambda_1$ but at the other wavelength $\lambda_2$ only one of the film layers absorbs the infrared rays. FIG. 9 shows the case where the both film layers absorb infrared rays at the both wavelengths $\lambda_1$ and $\lambda_2$ but at one of the wavelengths the absorption of one of the film layer is stronger than that of the other film layer and at the other wavelength the absorption of the latter is stronger than that of the former. FIG. 10 shows the case where the both film layers largely absorb infrared rays at the one wavelength $\lambda_1$ and at the other wavelength $\lambda_2$ absorb the infrared rays to the same as or lower than the absorption at the wavelength $\lambda_1$. As for the reference wavelength $\lambda_R$, it is most preferred to select the wavelength of infrared rays which are hardly absorbed by the both film layers but, in an unavoidable case, such a wavelength is selected which an absorption coefficient smaller than those of the both film layers at the sample wavelengths $\lambda_1$ and $\lambda_2$. The reference wavelength can be selected from a wavelength range close to both of the wavelengths $\lambda_1$ and $\lambda_2$ and, in addition, when the wavelengths $\lambda_1$, $\lambda_2$ and $\lambda_R$ can be detected by detectors of the same kind, it is sufficient only to select one common reference wavelength $\lambda_R$. Further, in the cases where the wavelengths $\lambda_1$ and $\lambda_2$ are spaced apart due to the combination of polymers, and where the wavelengths $\lambda_1$ and $\lambda_2$ cannot be detected by detectors of the same kind and must be detected separately by different kinds of detectors, different reference wavelengths may be set up in the vicinities of the wavelengths $\lambda_1$ and $\lambda_2$, respectively.

Further, in the case of using the reflector unit 48 as described previously in respect of FIG. 4, the positioning of the projector unit 11 and the reflector 48 relative to each other is easier than the alignment of the projector unit 11 and the photo detector unit 12 with each other, and in the case of achieving measurement while moving the measuring apparatus relative to the object being measured, even if a little change occurs on either side of the object to be measured, the measurement can be achieved with accuracy. On top of that, since infrared rays pass twice through the object to be measured, the absorption of infrared rays increases by that to enhance the SN ratio, permitting high precision measurement. Moreover, this invention needs neither contacting with the multilayer film to be measured nor destroying it and enables on-line measurement even in the case of the multilayer film to be measured being driven; therefore, this invention can be applied to a film thickness control apparatus employed in a multilayer film manufacturing process.

This invention will hereinbelow be described with reference to its experimental examples.

EXAMPLE 1

A multilayer film to be measured was a two-layer one whose film layers were respectively formed of polyethylene and polyvinylidene chloride. The construction of the measuring apparatus used was the same as shown in FIG. 1 and, as the light source 13, a tungsten lamp was lighted with a constant voltage. As the lenses 14 and 24, quartz lenses were used, and the light chopper 15 was driven by a synchronous motor 18 of 25 RPS at 50 Hz. The chromatic light of the reference wavelength $\lambda_R$ was obtained with the narrow-band, infrared band-pass interference filter 17R having a center transmission wavelength of $2.10\mu$ and a half power width of 80 m$\mu$. Similarly, the sample wavelength $\lambda_1$ was obtained with the narrow-band, infrared band-pass interference filter 17A having a center transmission wavelength $2.32\mu$ and a half power width of 80 m$\mu$, and the sample wavelength $\lambda_2$ was obtained with the narrow-band, infrared band-pass interference filter 17B having a center transmission wavelength of $2.40\mu$ and a half power width of 80 $\mu$m. As the detector 25, a PbS detector was used. The computer 53 was a Motorala's microcomputer, Model M6800. Actual film thickness variations of the multilayer film 12 that the polyethylene and polyvinylidene chloride film layers had set thicknesses of 94 $\mu$m and 8 $\mu$m, respectively, were measured. As a result of a comparison between the measured values thus obtained and those by visual observation, it was found that the film thicknesses were measured with accuracy of $\pm 1$ $\mu$m.

EXAMPLE 2

Figure 11:
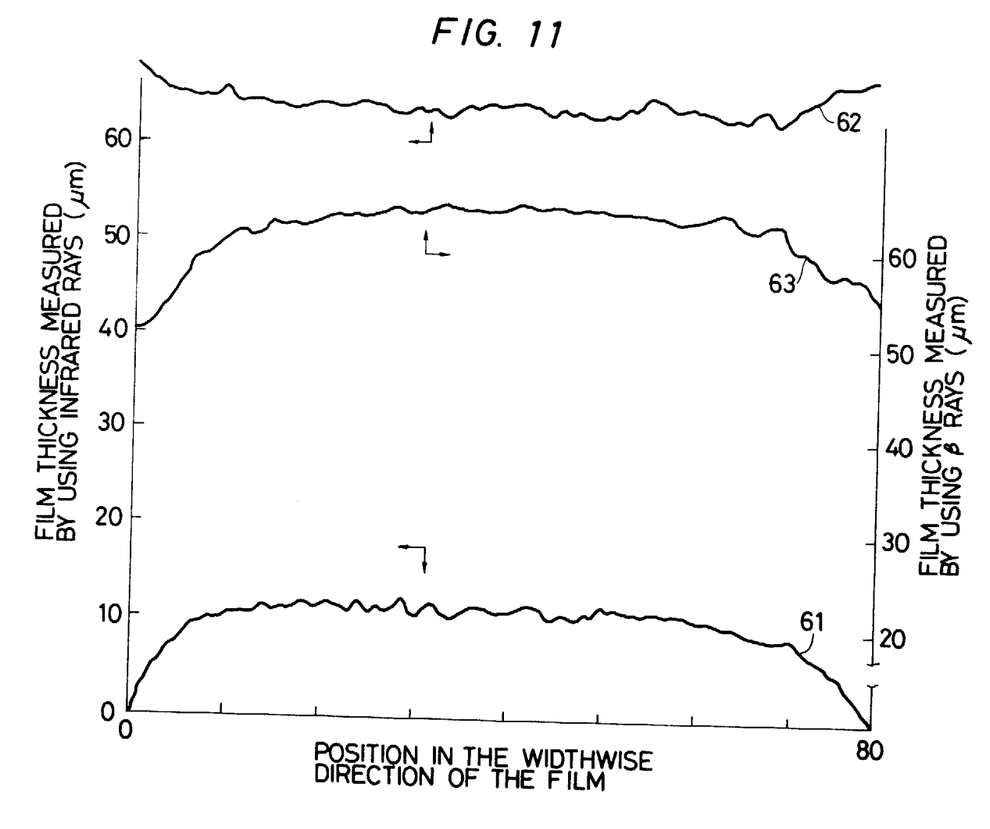
FIG. 11 is a graph showing the relationship of the measured film thickness to the position in the widthwise direction of the multilayer film.

The film thickness variations in the widewise direction of a multilayer film which was composed of polyethylene and polyvinylidene chloride film layers respectively having set thicknesses of 54 $\mu$m and 8 $\mu$m were measured, with a projector unit and a photo detector unit mounted on a travelling device. The measured values are shown in FIG. 11, the abscissa representing the position in the widthwise direction of the film, the left-hand ordinate the film thickness measured by using infrared rays and the right-hand ordinate the film thickness measured by using $\beta$ rays. The thickness of the polyvinylidene chloride layer measured by the thickness measuring apparatus of this invention is indicated by the curve 61 and the sum of the thicknesses of the polyvinylidene chloride and polyethylene layers is indicated by the curve 62. The total film thickness measured value obtained with a $\beta$-ray thickness gauge is indicated by the curve 63 for comparison. The polyvinylidene chloride film layer is very thin at both sides of the film but the total film thickness becomes a little large. The $\beta$-ray film thickness measurement is greatly affected by the thickness variations of the polyvinylidene chloride due to an essential film thickness error inherent to the $\beta$-ray measurement which results from larger specific gravity or polyvinylidene chloride than that of polyethylene, and the total thickness values measured by the $\beta$-ray thickness gauge is small at the both sides of the film to increase an error. The total thickness value obtained by measuring the actual total film thickness with a contacting differential transformer type dial gauge very well coincided with the measured value obtained by the infrared thickness gauge.

From the above two experimental examples, it will be seen that the present invention is very excellent.

It will be apparent that many modifications and variations may be effected without departing from the scope of novel concepts of this invention.

What is claimed is:

1. An infrared multilayered film thickness measuring method comprising the steps of:
   projecting an infrared ray including a plurality of sample wavelengths and at least one reference wavelength onto a composite multilayer film or sheet composed of a plurality of film layers of different synthetic resins, the infrared absorption wavelengths of each of the film layers coinciding with at least one of the sample wavelengths and the reference wavelength being selected not to coincide with the infrared absorption wavelength of each film layer;
   obtaining ratios between the amounts of infrared rays of the respective sample wavelengths transmitted through the multilayer film and the amount of infrared rays of the reference wavelength transmitted through the multilayer film;
   performing an operation for solving a simultaneous equation including the ratios and the infrared absorption coefficients of the film layers at the sample and reference wavelengths as coefficients and the thicknesses of the film layers as unknowns, thereby obtaining the thicknesses of the film layers.

2. An infrared multilayer film thickness measuring method according to claim 1, wherein a spectroscopically unseparated infrared ray is projected onto the multilayer film, and wherein an infrared ray transmitted through the multilayer film is separated into infrared monochromatic lights of the sample and reference wavelengths to detect the amounts of infrared lights of the respective wavelengths.

3. An infrared multilayer film thickness measuring method according to claim 1, wherein a spectroscopically unseparated infrared ray is projected onto the multilayer film, wherein an infrared ray reflected and scattered on the plane opposite from the plane of incidence of the multilayer film is separated into infrared monochromatic lights of the sample and reference wavelengths to detect the amounts of infrared lights of the respective wavelengths.

4. An infrared multilayer film thickness measuring method according to claim 1, wherein a spectroscopically unseparated infrared ray is projected onto the multilayer film, wherein an infrared ray transmitted through the multilayer film is reflected back to be retransmitted therethrough along substantially the same light path as that of the first transmission, wherein the infrared ray retransmitted through the multilayer film is separated into infrared monochromatic lights of the sample and reference wavelengths to detect the amounts of infrared lights of the respective wavelength.

5. An infrared multilayer film thickness measuring method according to claim 1, wherein spectroscopically preseparated infrared monochromatic lights of the sample and reference wavelengths are successively projected onto the multilayer film to successively detect the amounts of infrared lights of the respective wavelengths transmitted through the multilayer film.

6. An infrared multilayer film thickness measuring method according to claim 1, wherein spectroscopically preseparated infrared monochromatic lights of the sample and reference wavelengths are successively projected onto the multilayer film to successively detect the amounts of infrared lights of the respective wavelengths reflected by and scattered on the plane opposite from the plane of incidence of the multilayer film.

7. An infrared multilayer film thickness measuring method according to claim 1, wherein spectroscopically preseparated infrared monochromatic lights of the sample and reference wavelengths are successively projected onto the multilayer film, and wherein infrared rays transmitted through the multilayer film are reflected back to be retransmitted therethrough on substantially the same light paths as those of the first transmission, and wherein the amounts of infrared lights of the respective wavelengths retransmitted through the multilayer film are detected.

8. An infrared multilayer film thickness measuring method according to any one of claims 1 to 7, wherein only the infrared monochromatic lights of the sample and reference wavelengths are obtained by discretely separating the infrared ray spectroscopically.

9. An infrared multilayer film thickness measuring method according to any one of claims 1 to 7, wherein the infrared monochromatic lights of the respective wavelengths are obtained by continuously separating the infrared ray spectroscopically over an infrared wavelength range covering the infrared monochromatic lights of the sample and reference wavelengths.

10. An infrared multilayer film thickness measuring method according to any one of claims 1 to 7, wherein the amounts of infrared lights of the sample and reference wavelengths transmitted through the multilayer films are detected by a single photo detector on a time divided basis.

11. An infrared multilayer film thickness measuring apparatus comprising:
a projector unit for projecting an infrared ray including a plurality of sample wavelengths and at least one reference wavelength onto a composite multilayer film layers of different synthetic resins, the infrared absorption wavelength of each of the film layers coinciding with at least one of the sample wavelengths and the reference wavelength being selected not to coincide with the infrared absorption wavelength of each film layer;
a photo detector unit for receiving an infrared ray transmitted through the multilayer film at least once to detect the intensity of transmitted infrared light; and
an electrical processing unit for separating a light-intensity signal from the photo detector unit into sample signals indicating the intensity of infrared lights of the sample wavelengths and a reference signal indicating the intensity of the infrared light of the reference wavelength, obtaining ratios between the sample signals and the reference signal and solving a simultaneous equation including the ratios and the infrared absorption coefficients of the film layers at the sample and reference wavelengths as coefficients and the thicknesses of the film layers as unknowns, thereby obtaining the thicknesses of the film layers.

12. An infrared multilayer film thickness measuring apparatus according to claim 11, wherein the electrical processing unit comprises a processing part for processing the light-intensity signal detected by the photo detector unit to obtain the sample signals and the reference signal and an operation processing part for obtaining the ratios between the sample signals and the reference signal and solving a simultaneous equation including the ratios, and the infrared absorption coefficients of the film layers at the sample and reference wavelengths as coefficients and the thicknesses of the film layers as unknowns, thereby obtaining the thicknesses of the film layers.

13. An infrared multilayer film thickness measuring apparatus according to claim 11, which further comprises means for applying infrared rays of the respective wavelengths on a time divided basis to a single photo detector provided in the photo detector unit.

14. An infrared multilayer film thickness measuring apparatus according to claim 13, wherein the infrared applying means is arranged so that narrow-band, infrared band-pass interference filters respectively permitting the passage therethrough of infrared monochromatic lights of the sample and reference wavelengths are successively intercepted spectroscopically the unseparated infrared lights.

15. An infrared multilayer film thickness measuring apparatus according to claim 11, wherein the projector unit and the photo detector unit are disposed on both sides of the multilayer film.

16. An infrared multilayer film thickness measuring apparatus according to claim 11, wherein the projector unit and the photo detector unit are disposed on the same side with respect to the multilayer film, wherein the infrared ray projected from the projector onto the multilayer film is reflected and scattered on the plane on the opposite side from the plane of incidence of the multilayer film, and wherein the reflected and scattered light is received by the photo detector unit.

17. An infrared multilayer film thickness measuring apparatus according to claim 11, wherein the projector unit and the photo detector unit are disposed on the same side with respect to the multilayer film, wherein a reflector unit is disposed opposite the projector unit and the photo detector unit across the multilayer film, wherein the reflector unit reflects the infrared ray transmitted through the multilayer film back to be retransmitted therethrough along substantially the same light path as that of the first transmission, and wherein at least one portion of the transmitted light reflected from the reflector unit towards the projector unit is branched by a branch unit to be incident on the photo detector unit.

18. An infrared multilayer film thickness measuring apparatus according to claim 17, wherein the reflector unit is a corner cube.

19. An infrared multilayer film thickness measuring apparatus according to claim 11, wherein the operation processing unit includes a common logarithmic ratio circuit for obtaining the ratios.

20. An infrared multilayer film thickness measuring apparatus according to claim 11, wherein the projector unit is so arranged as to project an infrared monochromatic light over a certain infrared wavelength range while continuously changing its wavelength, and wherein the electrical processing unit includes means for separating the components of the sample and reference wavelength in synchronism with the continuous wavelength change of the infrared monochromatic light.

21. An infrared multilayer film thickness measuring apparatus according to claim 20, wherein the projector unit comprises a light source for producing a spectroscopically unseparated infrared ray, an infrared band-pass interference filter selecting the infrared ray, and means for changing the angle of incidence of the infrared ray to the infrared band-pass interference filter relative to each other.

* * * * *